(12) United States Patent
Wang et al.

(10) Patent No.: US 12,313,544 B2
(45) Date of Patent: May 27, 2025

(54) METHOD AND DEVICE FOR IDENTIFYING WASHING QUALITY OF FEATHER MATERIAL

(71) Applicant: KWONG LUNG ENTERPRISE CO., LTD., Taipei (TW)

(72) Inventors: Jui-Wen Wang, Taipei (TW); Yuan-Fu Lin, Taipei (TW); Chun-Hao Miao, Taipei (TW); Wei-Lun Lan, Taipei (TW); Che-Wei Chien, Taipei (TW)

(73) Assignee: KWONG LUNG ENTERPRISE CO., LTD., Taipei (TW)

( * ) Notice: Subject to any disclaimer, the term of this patent is extended or adjusted under 35 U.S.C. 154(b) by 259 days.

(21) Appl. No.: 17/873,963

(22) Filed: Jul. 26, 2022

(65) Prior Publication Data

US 2024/0035970 A1    Feb. 1, 2024

(51) Int. Cl.
*G01N 21/59* (2006.01)
*D06L 1/12* (2006.01)
*G01N 1/34* (2006.01)
*G01N 33/18* (2006.01)

(52) U.S. Cl.
CPC .............. *G01N 21/59* (2013.01); *D06L 1/12* (2013.01); *G01N 1/34* (2013.01); *G01N 33/18* (2013.01)

(58) Field of Classification Search
CPC . D06L 1/12; G01N 1/34; G01N 21/51; G01N 21/59; G01N 33/18
USPC .......................................................... 356/442
See application file for complete search history.

(56) References Cited

U.S. PATENT DOCUMENTS 4,169,706 A    10/1979    Kruchen

FOREIGN PATENT DOCUMENTS

| CN | 201340403 Y | * | 11/2009 |
| CN | 202994649 U | * | 6/2013 |
| CN | 206081896 U | * | 4/2017 |
| CN | 206240850 U |   | 6/2017 |
| CN | 212285081 U |   | 1/2021 |
| TW | 201938178 A |   | 10/2019 |
| TW | M634392 U |   | 11/2022 |
| WO | 2020101026 A1 |   | 5/2020 |

* cited by examiner

*Primary Examiner* — Sunghee Y Gray
(74) *Attorney, Agent, or Firm* — RABIN & BERDO, P.C.

(57) ABSTRACT

A method and device for identifying the washing quality of a feather material are applied to a feather material washing apparatus and essentially entail: a sampling unit that takes an appropriate amount of the water discharged from the feather material washing apparatus as a water sample, an impurity removing module that removes feather fiber and impurities that may compromise inspection accuracy, and a laser sensing device that senses, while the water sample is static, a transparency value of a portion of the water sample that extends across a predetermined distance, in order to identify the washing quality of a washed feather material. The method and device for identifying the washing quality of a feather material exercise intelligent judgment to enable a consistent standard, to ensure the efficiency and quality of a feather material washing procedure, and to reduce the associated costs.

9 Claims, 5 Drawing Sheets

METHOD AND DEVICE FOR IDENTIFYING WASHING QUALITY OF FEATHER MATERIAL

BACKGROUND OF THE INVENTION

1. Technical Field

The present invention relates to determination of the turbidity of water that has been used to wash a feather material and to identification of the washing quality. More particularly, the invention relates to a method and device for identifying the washing quality of a feather material, wherein the method and device for identifying the washing quality of a feather material exercise intelligent judgment to automatically determine the washing quality of a feather material and can produce consistent determination results.

2. Description of Related Art

One of the most important steps in processing a feather material is to wash the feather material with water, and the washing step is typically carried out after the feather material is sorted or classified. The term "feather material" is used herein to refer to either or both of down feathers and vaned feathers.

Currently, the parameters of such a washing process are set either by an experienced operator or in accordance with experimental data or the statistical result of data obtained in the past. However, as the amounts of oil and sand on feathers, among other variables, vary from one batch to another, good and consistent washing results are not guaranteed by basing the washing process parameters on experience or a reference database. In practice, a lot of labor and operational cost are required for checking the washing quality so that any portion that does not meet the washing requirement will be rewashed.

Moreover, it is common practice in the feather-related industries nowadays to assess the cleanliness of a feather material by observing the water turbidity in a glass tube. While this inspection method is easy to perform, it depends on the inspector's visual perception, meaning the method is highly subjective and lacks a consistent standard.

From the perspective of those engaging in the feather-related industries, therefore, there has yet to be a good mechanism for regulating the cleaning process, and thereby controlling the washing quality, of a feather material. Such mechanisms are called for to reduce the resources and cost required to ensure feather washing quality.

BRIEF SUMMARY OF THE INVENTION

The primary objective of the present invention is to exercise intelligent judgment by way of a specific means so as to eliminate the subjectivity of human judgement and achieve consistency in determining the washing quality of feather materials.

The present invention is fully applicable to the cleaning process of a feather material and the determination and management of washing quality, allows automation, makes it possible to adjust the cleaning process according to shipment requirements, can minimize the damage caused to the feather material by excessive washing, can reduce the consumption of water and electricity and hence the associated costs, and is therefore in line with the strategy of sustainable management.

From the perspective of those who engage in the cleaning of feather materials, the present invention not only can stabilize the quality of the cleaned feather materials and reduce repeated washing and customer complaints, but also allows an automated production and quality inspection mechanism to be established to greatly increase yield and work efficiency.

To achieve the aforesaid and other functions and objectives, the present invention provides a method for identifying the washing quality of a feather material. The method is applied to a feather material washing apparatus and includes the following steps as its main technical means and features: (a) completing the washing process of a feather material by the feather material washing apparatus; (b) driving a sampling unit to take an appropriate amount of the water discharged from the feather material washing apparatus as a water sample, and guiding the water sample to a water sample inspection area; (c) before the water sample gathers in the water sample inspection area, allowing the water sample to pass through an impurity removing module in order to filter out feather fiber and impurities that are in the water sample and are of sizes not smaller than about 1.2 mm; and (d) driving a laser sensing device to sense, while the water sample is static in the water sample inspection area, a transparency value of a portion of the water sample that extends across a predetermined distance, in order to identify the washing quality of the feather material after its washing process has been completed, wherein the laser sensing device is provided at the water sample inspection area.

Based on the technical concept of the present invention, a device for identifying the washing quality of a feather material is also provided. The device is configured to be provided in a feather material washing apparatus and includes a sampling unit, a water sample inspection area, an impurity removing module, a laser sensing device, and a main control unit as its technical means and structural features. The sampling unit is provided at a drain pipe of the feather material washing apparatus and is configured to take a water sample from the water discharged from the feather material washing apparatus. The water sample inspection area has a volume large enough to hold the water sample and is connected to the sampling unit in order to receive the water sample taken by the sampling unit. The impurity removing module is provided between the sampling unit and the water sample inspection area and includes at least one screen unit through which the water sample can pass in order to filter out feather fiber and impurities that are in the water sample and are of sizes not smaller than about 1.2 mm. The laser sensing device includes a transmitter unit and receiver unit that are provided at the water sample inspection area and are spaced apart from each other by a predetermined distance. The transmitter unit and the receiver unit are configured to emit and receive laser light respectively so as to sense a transparency value of a portion of the water sample that extends across the predetermined distance. The main control unit is in signal communication with the sampling unit and the laser sensing device and is configured to drive the sampling unit and the laser sensing device, in order for the sampling unit to take an appropriate amount of the water discharged from the feather material washing apparatus as the water sample when the feather material washing apparatus has completed the washing process of a feather material, and for the laser sensing device to sense, while the water sample is static in the water sample inspection area, the transparency value of the portion of the water sample that extends across the predetermined distance, thereby identifying the washing quality of the feather material after its washing process has been completed.

Preferably, the impurity removing module is provided with a box through which the water sample can pass downward, the screen unit is provided in the box, the box is wider at the top end than at the bottom end, and the box has a lateral side formed with at least one hollow groove that is not lower than the screen unit.

Preferably, the bottom side of the water sample inspection area is provided with a water sample discharging unit, and the water sample discharging unit is in signal communication with the main control unit and can be controlled by the main control unit in order to discharge the water sample after the transparency value is sensed.

Moreover, in one feasible embodiment of the foregoing method or device for identifying washing quality of feather material, the laser sensing device preferably uses visible laser light that has a wavelength of about 660 nm and can penetrate the water sample, the predetermined distance is preferably not greater than 300 mm, the impurity removing module is preferably provided with at least two screen units through which the water sample can pass, and each screen unit preferably has a mesh number not less than 16 (equivalent to having mesh openings smaller than 1.18 mm).

BRIEF DESCRIPTION OF THE SEVERAL VIEWS OF THE DRAWINGS

The aforesaid and other objectives, functions, and features of the present invention can be better understood by referring to the following detailed description of a preferred embodiment of the invention in conjunction with the accompanying drawings, in which.

DETAILED DESCRIPTION OF THE INVENTION

Referring to FIG. 1 to FIG. 4, the present invention relates mainly to a cleanliness determination technique that is applicable to a feather material washing apparatus 1. The related designs of the invention enable intelligent judgment and automation so as to achieve consistent judgment, ensure a desirable yield, and reduce a wasteful use of resources and energy.

Figure 1:
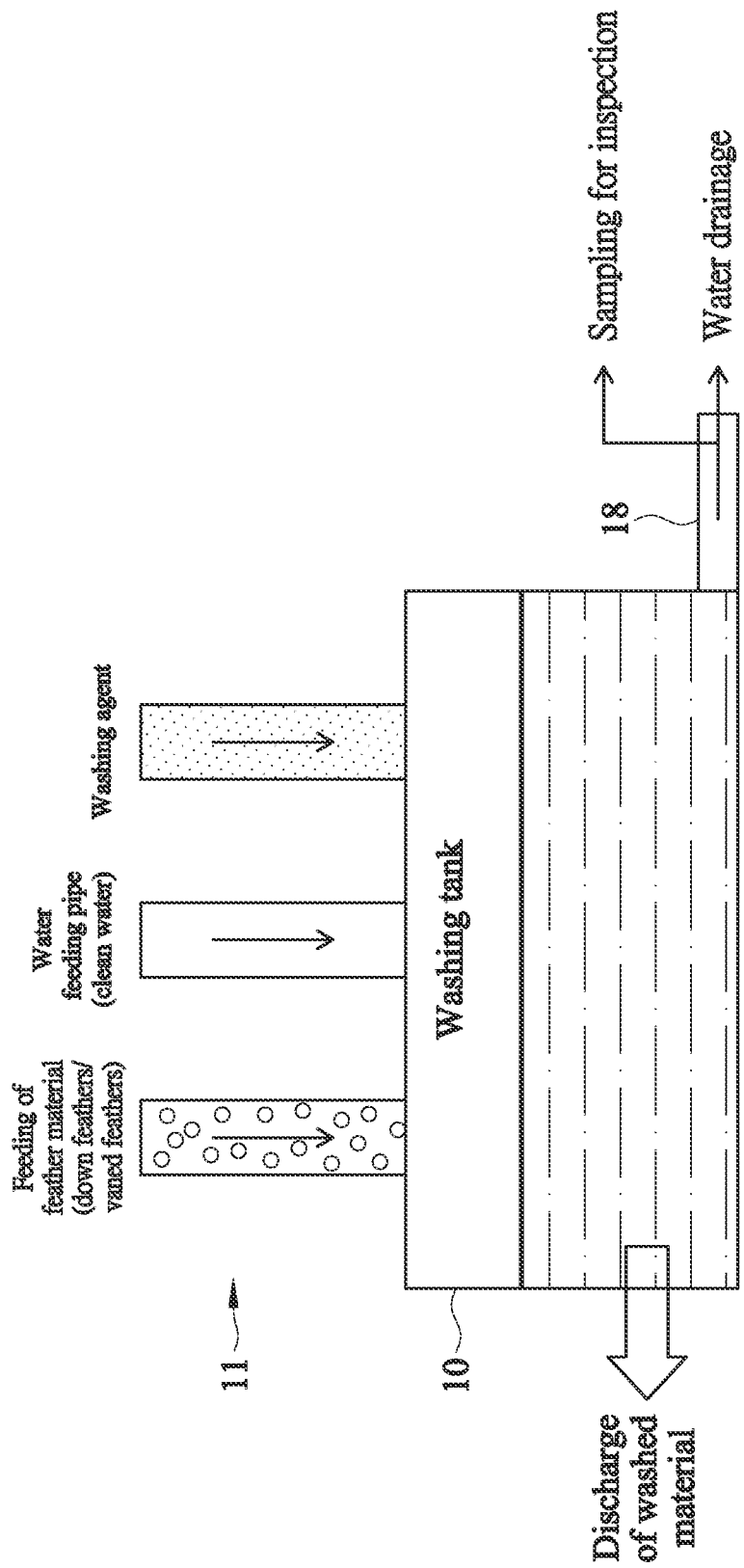
FIG. 1 schematically shows the washing tank of a feather material washing apparatus according to a preferred embodiment of the invention.

As shown in FIG. 1, the feather material washing apparatus 1 at least has a washing tank 10 in which a feather material can be washed. The washing tank 10 may be connected with a suitable material feeding mechanism 11 (e.g., a feather material feeding hopper, a water feeding pipe, a washing agent feeding hopper, and so on) and a drain pipe 18 through which water can be discharged from the feather material washing apparatus 1. The present invention essentially entails sampling and inspecting the water discharged from a washing process so that the cleanliness of a feather material that has been washed by the washing process can be determined by sensing the turbidity of the water sample taken.

It should be pointed out that, as is well known in the art, washing a feather material (be it down feathers or vaned feathers) with water can remove dirt and impurities from the feather material but may also damage the feather material, producing broken and detached feather fiber (e.g., broken down feathers and loose barbs); in other words, a certain percentage of loss of the feather material may result from the washing process. Consequently, the water used for washing is often full of foreign matter such as feather fiber and impurities, making it impossible to use the turbidity sensing device of a common washing apparatus (e.g., a washing machine). This is why the turbidity of the water used to wash a feather material is still determined nowadays by human observation and inspection. It remains a technical difficulty in the feather-related industries to achieve intelligent judgment of washing quality, to provide a consistent standard for the judgment, and to automate the judgment.

To overcome the aforesaid deficiencies of the prior art, the inventor of the present invention conducted a series of validations and comparisons through experimentation and finally succeeded in developing the method and device disclosed herein for identifying the washing quality of a feather material.

Figure 2:
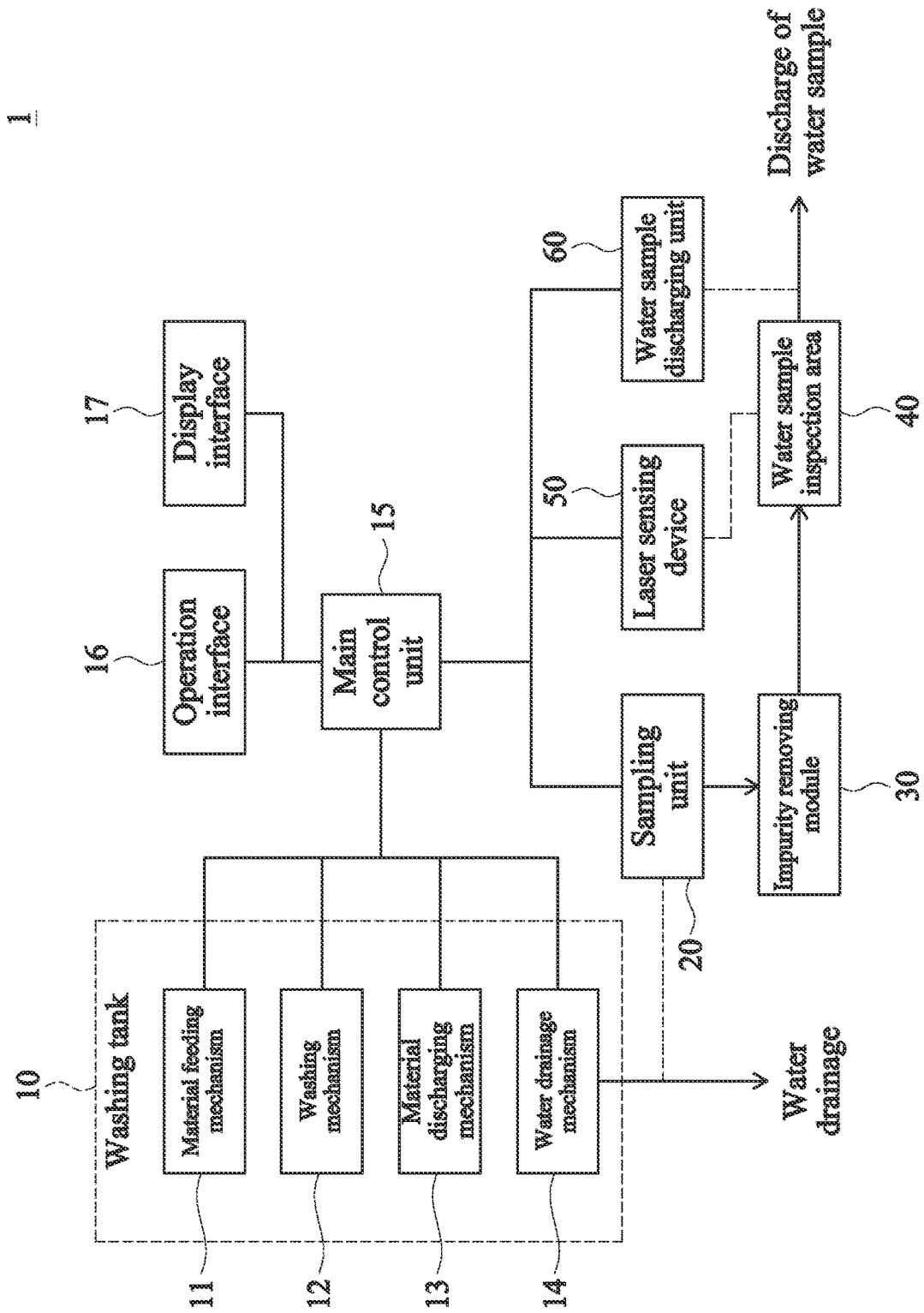
FIG. 2 is a block diagram of the entire feather material washing apparatus according to the preferred embodiment of the invention.

In the embodiment shown in FIG. 2, the feather material washing apparatus 1 further includes a material feeding mechanism 11, a washing mechanism 12, a material discharging mechanism 13, a water drainage mechanism 14, a main control unit 15, an operation interface 16, a display interface 17, a sampling unit 20, an impurity removing module 30, a water sample inspection area 40, a laser sensing device 50, and a water sample discharging unit 60.

The material feeding mechanism 11, the washing mechanism 12, the material discharging mechanism 13, and the water drainage mechanism 14 are separately connected to or provided at the washing tank 10 and are controlled by the main control unit 15 in order to perform such automated functions as feeding a feather material, adding water, adding a washing agent, washing, dewatering, draining, and discharging the washed feather material.

The operation interface 16 and the display interface 17 are respectively an interface through which a user can make operation-related settings and an interface for displaying the related information so that the main control unit 15 can carry out an automated operation based on the parameters set by the user. In one feasible embodiment, the operation interface 16 and the display interface 17 may be integrated as a touch-controlled display unit having the functions of both interfaces or even as a remotely connected touch-controlled display unit.

Figure 3:
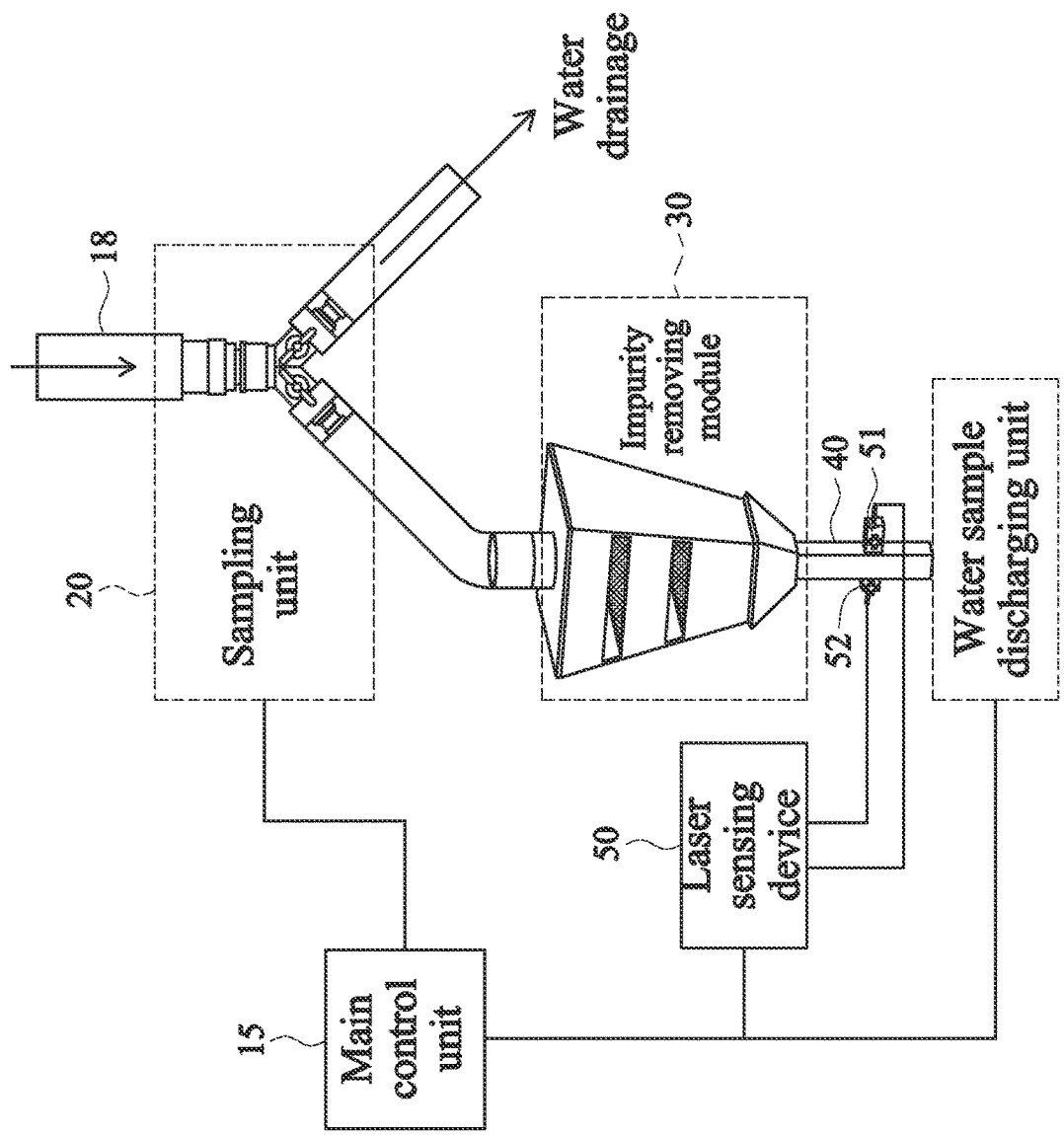
FIG. 3 is a schematic drawing of a device for identifying the washing quality of a feather material according to the preferred embodiment of the invention.

The sampling unit 20, the impurity removing module 30, the water sample inspection area 40, the laser sensing device 50, and the water sample discharging unit 60 are the major parts of the illustrated embodiment that are related to the identification of the washing quality of a feather material. As shown in FIG. 3, the sampling unit 20 may be a diverter valve provided at a drain pipe 18 of the feather material washing apparatus 1 and serves mainly to take a to-beinspected water sample from the water discharged from the feather material washing apparatus 1. The impurity removing module 30 is provided between the sampling unit 20 and the water sample inspection area 40 and essentially includes at least one screen unit 31 (see FIG. 5 and FIG. 6) through which the water sample can pass, and which is configured to filter out feather fiber and impurities that are in the water sample and at least about 1.2 mm in size. The water sample inspection area 40 has a volume large enough to hold the water sample and serves mainly to receive the water sample taken by the sampling unit 20. The laser sensing device 50 essentially includes a transmitter unit 51 and a receiver unit 52. The transmitter unit 51 and the receiver unit 52 are provided at the water sample inspection area 40, are spaced apart from each other by a predetermined distance, and are configured to emit and receive laser light respectively so as to sense a transparency value of a portion of the water sample that extends across the predetermined distance. The water sample discharging unit 60 may be a shut-off valve, is provided on the bottom side of the water sample inspection area 40, and serves mainly to discharge the water sample after the transparency value is sensed.

The main control unit 15 is in signal communication with the sampling unit 20, the laser sensing device 50, and the water sample discharging unit 60 and is configured to drive the sampling unit 20, the laser sensing device 50, and the water sample discharging unit 60 in a timely manner. More specifically, the sampling unit 20 can be driven to take an appropriate amount of the water discharged from the feather material washing apparatus 1 as a water sample when the feather material washing apparatus 1 has completed the washing process of a feather material; the laser sensing device 50 can be driven, when the water sample is static in the water sample inspection area 40, to sense the transparency value of a portion of the water sample that extends across the predetermined distance, in order to identify the washing quality of the feather material after its washing process has been completed; and the water sample discharging unit 60 can be controlled to discharge the water sample after the transparency value is sensed.

Figure 4:
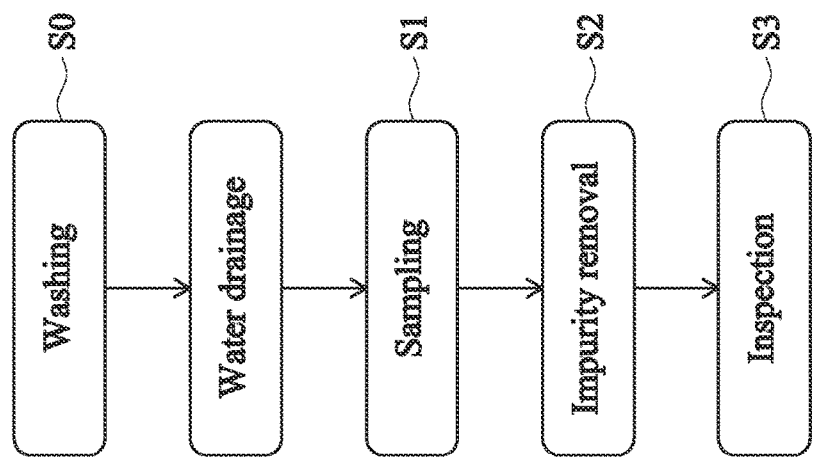
FIG. 4 is the flowchart of a method for identifying the washing quality of a feather material according to the preferred embodiment of the invention.

The major parts of the process flow of identifying the washing quality of a feather material according to this embodiment are shown in FIG. 4. To begin with, the feather material washing apparatus 1 completes the washing process of a feather material (step S0). When water is subsequently discharged from the feather material washing apparatus 1, the sampling unit 20 is driven to take an appropriate amount of the discharged water as a water sample (step S1) and guide the water sample to the water sample inspection area 40. Before the water sample gathers in the water sample inspection area 40, an impurity removing process (step S2) is performed, during which process the water sample passes through the impurity removing module 30 such that feather fiber and impurities in the water sample, in particular those whose sizes are about 1.2 mm or above, are filtered out. The water sample then gathers in the water sample inspection area 40. When the water sample becomes static in the water sample inspection area 40, the laser sensing device 50 is driven to perform an inspection (step S3), i.e., to sense the transparency value of a portion of the water sample that extends across the predetermined distance. This transparency value can be used as the basis on which to identify the washing quality of the feather material after its washing process has been completed.

In this embodiment, the IB-05 Thrubeam-Type Laser Detection Sensor of Keyence is used as the major part of the laser sensing device 50. The IB-05 sensor can sense water samples not wider than 300 mm with visible laser light whose wavelength is about 660 nm, and can thereby obtain transparency values accurately and consistently. Each transparency value sensed by the laser sensing device 50 can be correlated to the actual turbidity through a cross comparison and by setting and adjusting the deviation properly and can therefore serve as an accurate reference for identifying washing quality. Besides, according to actual test results of the laser sensing device 50, only when strong light (e.g., search light) is projected directly to the receiver unit 52 will the sensing of a water sample be adversely affected. It follows that the water sample inspection area 40 does not require an additional light blocking structure, meaning the present invention can work stably in an environment that has normal lighting.

Figure 6:
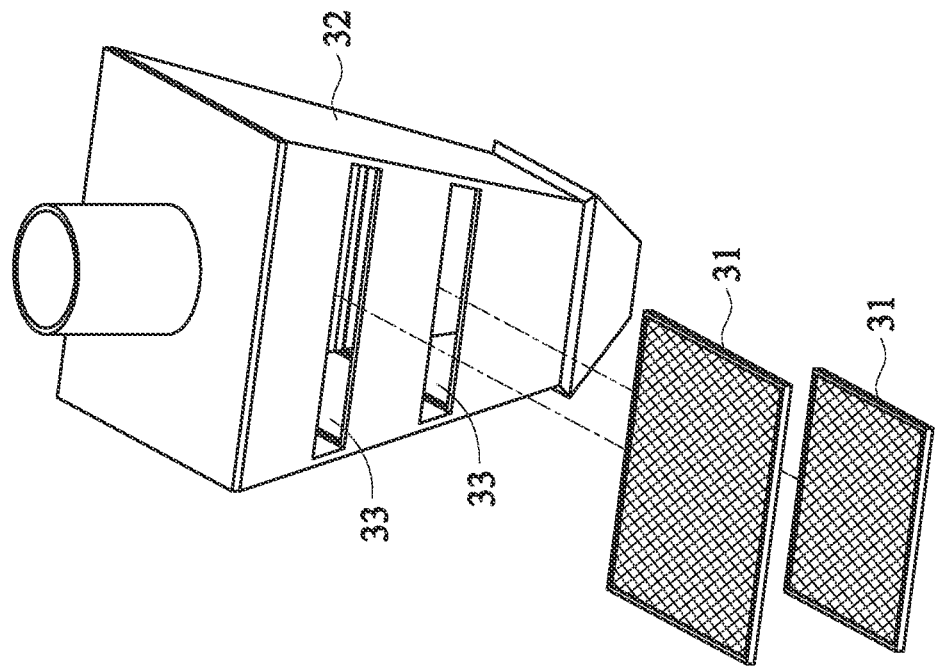
FIG. 6 is another structural diagram of the impurity removing module in the preferred embodiment of the invention.
Figure 5:
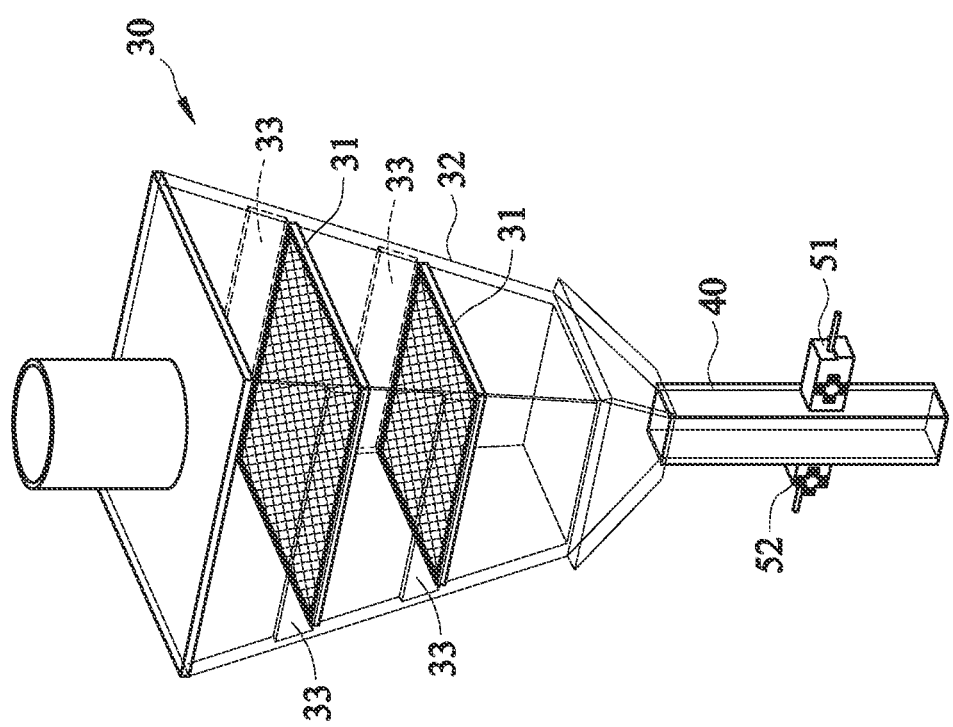
FIG. 5 schematically shows the structure of the impurity removing module in the preferred embodiment of the invention.

Referring to FIG. 5 and FIG. 6, the impurity removing module 30 in this embodiment is structured as a box 32 that is generally wider at the top end than at the bottom end, and that is provided with two screen units 31 through which a water sample can pass. Each screen unit 31 has a mesh number not less than 16 (equivalent to having mesh openings smaller than 1.18 mm) so as to effectively filter out impurities and feather fiber that may affect the sensing operation of the laser sensing device 50, the objective being to ensure the accuracy of the sensing result. In addition, the box 32 is so configured that a water sample flows through the box 32 in a downward direction, and that two lateral sides of the box 32 are each formed with two hollow grooves 33 that are slightly higher than the two screen units 31 respectively to facilitate the cleaning and replacement of each screen unit 31. It is even feasible for the feather fiber filtered out to be recycled in order to reduce the loss of feather material caused by washing with water (the recycling is typically carried out for down feathers).

Figure 7:
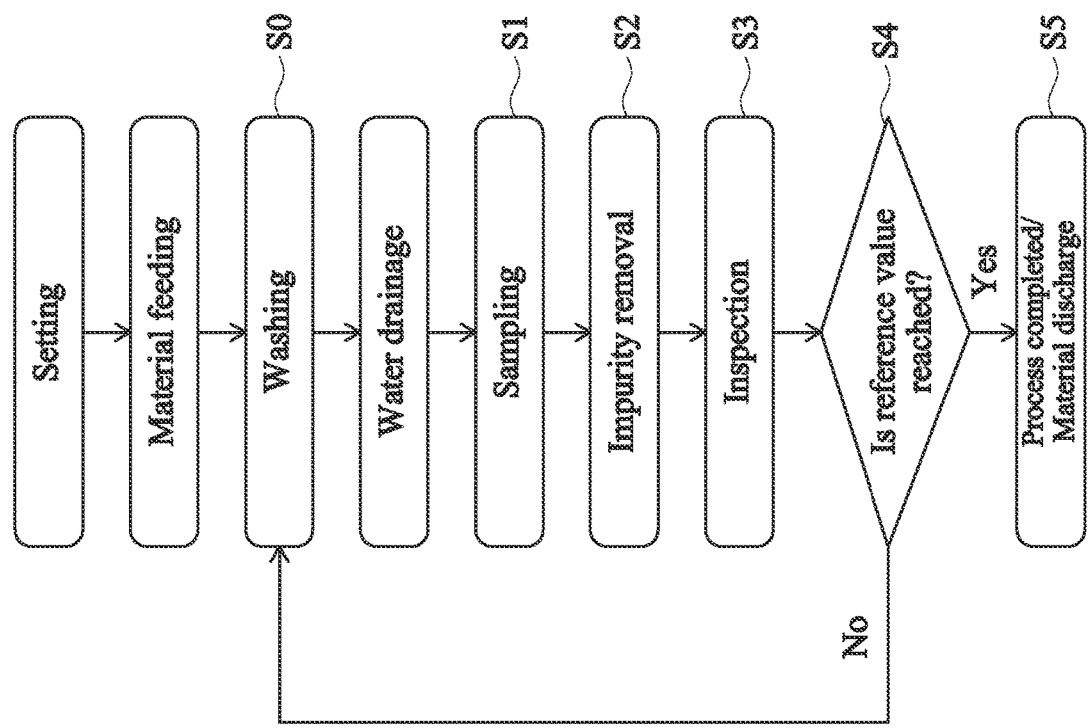
FIG. 7 is the flowchart of an automated washing process based on the preferred embodiment of the invention.

Once applied to the feather material washing apparatus 1, the present invention can produce such effects as allowing the identification of washing quality to be automated, performed consistently through intelligent judgment, and energy-saving. Referring to FIG. 7 for the flowchart of an automated washing process based on the invention, a user can set the related parameters and the desired reference value (i.e., the desired cleanliness parameter) in advance. After the feather material washing apparatus 1 is started, the main control unit 15 performs a material feeding step according to the preset parameters by driving the feeding mechanism 11 to transfer a predetermined amount of feather material into the washing tank 10. The washing step S0 is then carried out, with the feeding mechanism 11 driven again to add water and a washing agent into the washing tank 10 at predetermined ratios, and the washing mechanism 12 driven to perform a washing operation. When the washing operation is completed, the water drainage mechanism 14 is driven to dewater the feather material and drain the washing tank 10. During the draining process, the sampling unit 20 is driven to perform the sampling step S1, in which an appropriate amount of the water discharged from the washing tank 10 is taken as a water sample. The water sample flows through the impurity removing module 30 to complete the impurity removing step S2, in which the impurity removing module 30 filters out feather fiber and impurities that are in the water sample and whose sizes are about 1.2 mm or above. Following that, the filtered water sample gathers in the water sample inspection area 40, where the inspection step S3 is carried out. In this step, the main control unit 15 drives the laser sensing device 50 into operation a predetermined amount of time after the sampling unit 20 has been driven (the water sample inspection area 40 may also be provided with a suitable sensor whose sensing result determines when to activate the related components). The laser sensing device 50 senses the transparency value of the water sample while the water sample is static. (The sensing value will fluctuate if the water sample is not static, and a built-in program can be used to identify whether the sensing value is stable, i.e., whether the water sample is static.) Once the transparency value is sensed, the main control unit 15 compares the transparency value against the preset reference value (step S4) and drives the water sample discharging unit 60 to discharge the water sample. If the reference value is reached, indicating that the cleanliness of the washed feather material meets the standard, step S5 will be performed to determine that the feather material has been thoroughly washed, and to drive the material discharging mechanism 13 to output the feather material. If the reference value is not reached, indicating that the cleanliness of the washed feather material does not meet the standard, the process flow will return to the washing step S0, with the related mechanisms driven again to carry out another washing operation. The washing, water drainage, sampling, impurity removing, and inspection steps can be conducted repeatedly until the inspection result reaches the reference value.

According to the above, the present invention enables accurate quality control during an automated feather material washing process. Unnecessary steps of the washing process are reduced to advantageously save water and electricity and minimize the loss of raw materials. The invention, therefore, has solved the aforesaid technical difficulty in the feather-related industries and satisfies the patentability requirements. It should be understood, however, that the embodiment described above is only a preferred one of the invention, and that any extension, modification, simple change, or equivalent substitution based on the technical means of the invention shall fall within the scope of the appended claims.

What is claimed is:

1. A device for identifying washing quality of a feather material, the device being provided in a feather material washing apparatus and comprising:
   a diverter valve provided at a drain pipe of the feather material washing apparatus and configured to take a water sample from water discharged from the feather material washing apparatus;
   a water sample inspection area having a volume large enough to hold the water sample, the water sample inspection area being connected to the diverter valve in order to receive the water sample taken by the diverter valve;
   an impurity removing filter provided between the diverter valve and the water sample inspection area and including at least one screen comprising a mesh allowing passage of the water sample in order to filter out feather fiber and impurities that are in the water sample and are of sizes not smaller than about 1.2 mm;
   a laser sensing device including a transmitter unit and receiver unit, wherein the transmitter unit and the receiver unit are provided at the water sample inspection area, spaced apart from each other by a predetermined distance, and configured to emit and receive laser light respectively so as to sense a transparency value of a portion of the water sample that extends across the predetermined distance; and
   a main control unit in signal communication with, and configured to drive, the diverter valve and the laser sensing device, in order for the diverter valve to take an appropriate amount of the water discharged from the feather material washing apparatus as the water sample when the feather material washing apparatus has completed a washing process of the feather material, and for the laser sensing device to sense, while the water sample is static in the water sample inspection area, the transparency value of the portion of the water sample that extends across the predetermined distance, thereby identifying the washing quality of the feather material after the washing process thereof has been completed.

2. The device for identifying washing quality of feather material of claim 1, wherein the laser sensing device uses visible laser light having a wavelength of about 660 nm and capable of penetrating the water sample.

3. The device for identifying washing quality of feather material of claim 2, wherein the predetermined distance is at most 300 mm.

4. The device for identifying washing quality of feather material of claim 3, wherein the impurity removing filter includes at least two said screens allowing passage of the water sample, and each said screen has a mesh number not less than 16.

5. The device for identifying washing quality of feather material of claim 3, wherein the impurity removing filter is provided with a box allowing downward passage of the water sample, the screen is provided in the box, the box is wider at a top end of the box than at a bottom end of the box, and the box has a lateral side formed with at least one hollow groove not lower than the screen.

6. The device for identifying washing quality of feather material of claim 3, wherein the water sample inspection area has a bottom side provided with a water sample discharging unit, and the water sample discharging unit is in signal communication with and controllable by the main control unit in order to discharge the water sample after the transparency value is sensed.

7. The device for identifying washing quality of feather material of claim 1, wherein the impurity removing filter includes at least two said screens allowing passage of the water sample, and each said screen has a mesh number not less than 16.

8. The device for identifying washing quality of feather material of claim 1, wherein the impurity removing filter is provided with a box allowing downward passage of the water sample, the screen is provided in the box, the box is wider at a top end of the box than at a bottom end of the box, and the box has a lateral side formed with at least one hollow groove not lower than the screen.

9. The device for identifying washing quality of feather material of claim 1, wherein the water sample inspection area has a bottom side provided with a water sample discharging unit, and the water sample discharging unit is in signal communication with and controllable by the main control unit in order to discharge the water sample after the transparency value is sensed.

* * * * *